(12) United States Patent
Rho et al.

(10) Patent No.: US 11,464,787 B2
(45) Date of Patent: Oct. 11, 2022

(54) COMPOSITION COMPRISING OLEANOLIC ACID ACETATE AS ACTIVE INGREDIENT FOR PREVENTING, ALLEVIATING, OR TREATING RENAL TOXICITY INDUCED BY MEDICINE

(71) Applicant: Korea Research Institute of Bioscience and Biotechnology, Daejeon (KR)

(72) Inventors: Mun Chual Rho, Daejeon (KR); Seung Woong Lee, Daejeon (KR); Soyoung Lee, Daejeon (KR); Sang-Hyun Kim, Daegu (KR); Kwon Moo Park, Daegu (KR); Woo Song Lee, Daejeon (KR); Kyungsook Jung, Daejeon (KR); Chan Sun Park, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 16/339,130

(22) PCT Filed: Sep. 29, 2017

(86) PCT No.: PCT/KR2017/011044
§ 371 (c)(1),
(2) Date: Apr. 3, 2019

(87) PCT Pub. No.: WO2018/066954
PCT Pub. Date: Apr. 12, 2018

(65) Prior Publication Data
US 2020/0046728 A1 Feb. 13, 2020

(30) Foreign Application Priority Data
Oct. 4, 2016 (KR) .......................... 10-2016-0127536

(51) Int. Cl.
A61K 31/56 (2006.01)
A61P 13/12 (2006.01)
A61K 33/243 (2019.01)

(52) U.S. Cl.
CPC .............. *A61K 31/56* (2013.01); *A61P 13/12* (2018.01); *A61K 33/243* (2019.01)

(58) Field of Classification Search
None
See application file for complete search history.

(56) References Cited

U.S. PATENT DOCUMENTS

2014/0179780 A1 6/2014 Rho et al.

FOREIGN PATENT DOCUMENTS

| CN | 103648502 A | 3/2014 |
|---|---|---|
| JP | 2010105937 A | 5/2010 |
| JP | 2014-516939 A | 7/2014 |
| KR | 10-1993-0021201 A | 11/1993 |
| KR | 10-2003-0082763 A | 10/2003 |
| KR | 10-2007-0026898 A | 3/2007 |
| KR | 10-2012-0124361 A | 11/2012 |
| KR | 10-1737277 B1 | 5/2017 |

OTHER PUBLICATIONS

Ozkok et al., "Pathophysiology of Cisplatin-Induced Acute Kidney Injury", BioMed Research International, vol. 2014, Article ID 967826, 17 pages, 2014. (Year: 2014).*
Takeshi et al., Machine English translation of JP 2010105937 A patent publication. (Year: 2010).*
Miller, R. et al., Mechanisms of Cisplatin Nephrotoxicity, Toxins 2010, 2, pp. 2490-2518.
Mishra, S. et al., Antioxidant and anti infective potential of Oleanolic acid acetate vis-a-vis Vitec negundo Linn. And Droxylum indicum Vent. Against human pathogens causing infections of UT, GIT, and skin, Orient Pharm Exp Med, 2015, 15, pp. 73-82.
Maniya, et al., World J. Pharm. Pharm. Sci. (2014) vol. 3, Issue 3, 1677-1687.
PCT International Search Report and Written Opinion dated Jan. 15, 2019 in corresponding Application No. PCT/KR2017/011044, 21 pages.
Allah, O. M. et al., Effect of Combined Fenofibrate and Nicotinamide on Oxidative Stress and Inflammatory Cytokines Involved in Cisplatin-Induced Nephrotoxicity in Rats, American Journal of Pharmacology and Toxicology, 2014, vol. 9, Issue 4, p. 206-222.
Ramesh, G et al., TNF-α mediates chemokine and cytokine expression and renal injury in cisplatin nephrotoxicity, The Journal of Clinical Investigation, 2002, vol. 110, No. 6, p. 835-842.
Yoo K. H. et al., 3-0-Acetyloleanolic acid induces apoptosis in human colon carcinoma Hct-116 cells, Phytotherapy Research, 2012, pp. 1541-1546.
European Search Report from EPO Patent Office in Application No. 17858748.1 dated May 4, 2020.
Miller, Ronald P. et al, Mechanisms of Cisplatin Nephrotoxicity, www.mdpi.com/journal/toxins, 2010, pp. 2490-2518.

* cited by examiner

*Primary Examiner* — Savitha M Rao
*Assistant Examiner* — Gregg Polansky
(74) *Attorney, Agent, or Firm* — Dilworth IP, LLC

(57) ABSTRACT

The present invention relates to a composition for preventing, improving or treating drug-induced nephrotoxicity, the composition comprising oleanolic acid acetate as an active ingredient. More specifically, the present invention relates to a pharmaceutical composition for preventing or treating drug-induced nephrotoxicity comprising oleanolic acid acetate or a pharmaceutically acceptable salt thereof as an active ingredient, a health functional food for preventing or improving drug-induced nephrotoxicity comprising the active ingredients, and an anticancer adjuvant comprising the active ingredients. The oleanolic acid acetate of the present invention is derived from a natural product and has no side effects and no cytotoxicity and has excellent effects of preventing, improving and treating nephrotoxicity caused by a drug, particularly a platinum-based anticancer drug, so that it can be utilized as a pharmaceutical composition, a health functional food, and a cancer adjuvant thereof.

4 Claims, 7 Drawing Sheets

COMPOSITION COMPRISING OLEANOLIC ACID ACETATE AS ACTIVE INGREDIENT FOR PREVENTING, ALLEVIATING, OR TREATING RENAL TOXICITY INDUCED BY MEDICINE

TECHNICAL FIELD

The present invention relates to a composition for preventing, improving or treating drug-induced nephrotoxicity, the composition including oleanolic acid acetate as an active ingredient.

More specifically, the present invention relates to a pharmaceutical composition for preventing or treating drug-induced nephrotoxicity including oleanolic acid acetate or a pharmaceutically acceptable salt thereof as an active ingredient, a health functional food for preventing or improving drug-induced nephrotoxicity including the active ingredients, and an anticancer adjuvant including the active ingredients. Provided also are a method of treating drug-induced nephrotoxicity using oleanolic acid acetate or a pharmaceutically acceptable salt thereof, a method of treating cancer using oleanolic acid acetate or a pharmaceutically acceptable salt thereof and platinum-based anticancer drug, and various uses of oleanolic acid acetate or a pharmaceutically acceptable salt thereof.

BACKGROUND

It is estimated that around 14 million people develop cancer worldwide and about 8.2 million deaths from cancer. In Korea, cancer has been the leading cause of death since 1983, and 28.3% of all deaths in 2013 have been cancer-related deaths (National Cancer Center, Korea 2012).

Currently, various methods such as surgery, radiation therapy, and gene therapy are used to treat cancer. However, chemotherapy which uses anticancer drugs is one of the most commonly used treatments. As a representative anticancer drug, Cisplatin (or cis-diamine-dichloroplatinum [II]) is one of platinum-based anticancer drug and widely used in clinical practice as a chemotherapeutic agent for treating ovarian cancer, bladder cancer, lung cancer, head and neck cancer, testicular cancer, and the like.

Cisplatin is known to produce active oxygen species, thereby attacking cancer cells and induce DNA inter-intrastrand cross-linking and the DNA adduct formation in cancer cells, thereby showing anticancer effects. Thus, Cisplatin has been known to inhibit DNA replication of cancer cell which cell division is strong to show anticancer effect (Boulikas T., Oncology Rep, 10:1663-1682, 2003). However, side effects such as bone marrow suppression, gastrointestinal toxicity, neurotoxicity, nephrotoxicity and hepatotoxicity have been reported, and the nephrotoxicity among these side effects is recognized as the biggest problem. Cisplatin is known to accumulate intensely in the kidneys and to increase the accumulation in proportion to the dose administered, leading to severe toxicity (Safirstein R., Am J Kidney Dis 8:356-367, 1986).

Because 25% to 35% of patients treated with cisplatin have been shown to cause nephrotoxicity in clinical practice, pharmacological approaches to reduce this toxicity are being studied (Merouani A., Am J Nephrol 17:53-58, 1997). In addition, experimental evidence has been reported to interpret the pathophysiological mechanism of nephrotoxicity by cisplatin as a change in inflammatory response, and research on inflammation-related factors associated with the regulation of nephrotoxicity has been conducted (Ramesh G., J Clin Invest 110: 835-842, 2002). In addition, the acute renal failure toxicity caused by the anticancer drug is toxic due to the nephrotoxin, and the same toxicity can be detected while using antibiotics. Accordingly, the inhibitor of nephrotoxicity by cisplatin is considered to be effective for the antibiotic-induced nephrotoxicity.

Under these circumstances, the present inventors have made intensive efforts to find a substance for preventing or treating nephrotoxicity caused by a drug, particularly a platinum-based anticancer drug. As a result, it has been identified and proved that, in an animal model, oleanolic acid acetate inhibits nephrotoxicity induced by acute renal failure caused by a platinum-based anticancer drug. Thus, the present inventors completed the invention related to the composition for preventing, improving or treating drug-induced nephrotoxicity and an anticancer adjuvant using the same.

SUMMARY OF THE INVENTION

The present invention aims to provide a composition for preventing, improving or treating nephrotoxicity, the composition including oleanolic acid acetate.

More specifically, an object of the present invention is to provide a pharmaceutical composition for preventing or treating drug-induced nephrotoxicity, including oleanolic acid acetate or a pharmaceutically acceptable salt thereof as an active ingredient.

Another object of the present invention is to provide a health functional food for preventing or improving drug-induced nephrotoxicity, including oleanolic acid acetate or a sitologically acceptable salt thereof as an active ingredient.

Still another object of the present invention is to provide an anticancer adjuvant for preventing or treating anticancer drug-induced nephrotoxicity, including oleanolic acid acetate or a pharmaceutically acceptable salt thereof as an active ingredient.

Yet another object of the present invention is to provide a method of treating drug-induced nephrotoxicity by administering to a patient a pharmaceutically effective amount of oleanolic acid acetate or a pharmaceutically acceptable salt thereof.

Yet another object of the present invention is to provide a use of oleanolic acid acetate or a pharmaceutically acceptable salt thereof in the preparation of the drug for treating drug-induced nephrotoxicity.

Yet another object of the present invention is to provide a composition including oleanolic acid acetate or a pharmaceutically acceptable salt thereof used for treating drug-induced nephrotoxicity.

Yet another object of the present invention also is to provide a use of oleanolic acid acetate or a pharmaceutically acceptable salt thereof used for treating drug-induced nephrotoxicity.

Yet another object of the present invention is to provide a method of treating cancer by administering to a patient a pharmaceutically effective amount of oleanolic acid acetate or a pharmaceutically acceptable salt thereof as an anticancer adjuvant and a pharmaceutically effective amount of a platinum-based anticancer drug.

Yet another object of the present invention is to provide a use of oleanolic acid acetate or a pharmaceutically acceptable salt thereof in the preparation of the anticancer adjuvant.

Yet another object of the present invention is to provide a composition including oleanolic acid acetate or a pharmaceutically acceptable salt thereof for a use as an anticancer adjuvant.

Yet another object of the present invention is to provide a use of oleanolic acid acetate or a pharmaceutically acceptable salt thereof for an anticancer adjuvant.

DESCRIPTION OF THE INVENTION

In order to solve the above-mentioned problems, the present invention provides, as one embodiment, a pharmaceutical composition for preventing or treating drug-induced nephrotoxicity, the composition including oleanolic acid acetate, a compound represented by the following chemical formula I or a pharmaceutically acceptable salt thereof as an active ingredient.

Chemical Formula I

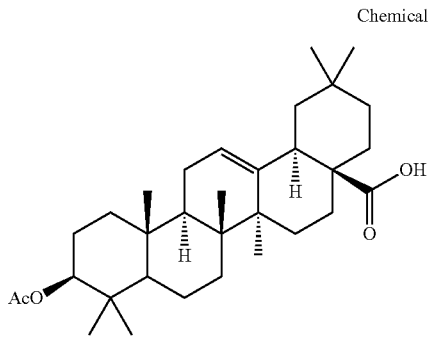

The present inventors firstly found that oleanolic acid acetate improves the drug-induced nephrotoxicity and particularly has confirmed that according to one embodiment of the present invention, oleanolic acid acetate effectively reduces BUN values (FIG. 2D), inflammatory cytokine (TNF-α, IL-6) levels in blood (FIGS. 3A and 3B), inflammatory factor (TNF-α, IL-6, COX-2 and MCP-1) expression levels in kidney tissue (FIGS. 4A, 4B, 4C and 4D), which are indicators of renal function in animal models of acute renal failure induced by Cisplatin, which is one of platinum-based anticancer drugs. Accordingly, the oleanolic acid acetate of the present invention is considered to have the same effects on other platinum-based anticancer drugs, for example, carboplatin, oxaliplatin and nedaplatin, or antibiotics such as aminoglycoside, tetracycline, sulfa drug, gentamicin, which have similar action mechanism of inducing nephrotoxicity as well as cisplatin.

Further, in one embodiment of the present invention, oleanolic acid acetate is significantly less cytotoxic than oleanolic acid, and thus has no side effects when applied to an animal or a human body, and thus it can be used variously for preventing, improving and treating nephrotoxicity.

The oleanolic acid acetate of the present invention can be obtained by a commercially available compound or a well-known method. According to one embodiment of the present invention, the present inventors have isolated and purified the oleanolic acid acetate of the present invention from adzuki beans. Specifically, the ethanol extract of adzuki beans is fractionated with hexane to obtain a hexane soluble fraction. This is separated by silica gel column chromatography using a mixed solvent of hexane and ethyl acetate, and then recrystallized using methanol to isolate the pure oleanolic acid acetate compound represented by the following chemical formula I.

Chemical Formula I

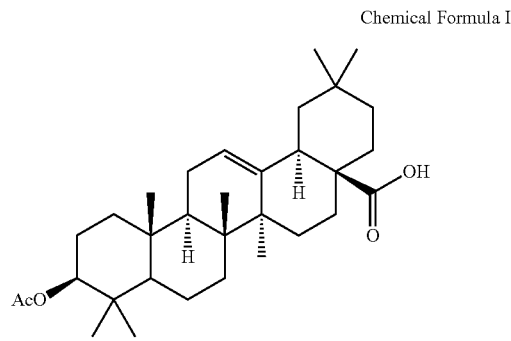

As used herein, the term "drug-induced nephrotoxicity" refers to damage to the kidneys induced by the use of drugs used for diagnostic or therapeutic purposes. The administered drugs may reduce blood flow into the kidneys, inhibit the function of the glomeruli and tubules, resulting in damage to the kidneys, necrosis in the proximal tubules, and severe renal failure depending on the severity. Any of the drugs that cause nephrotoxicity is included within the scope of the present invention. The drugs may include, for example, platinum-based anticancer drugs such as at least one selected from the group consisting of cisplatin, carboplatin, oxaliplatin and nedaplatin and include antibiotics similar in nephrotoxicity inducing mechanism such as at least one selected from the group consisting of aminoglycoside, tetracycline, sulfa drug, and gentamicin.

The pharmaceutical composition including the compound of the chemical formula I or a pharmaceutically acceptable salt thereof of the present invention may further include an appropriate carrier, excipient or diluent conventionally used in the production of a pharmaceutical composition. In this regard, the content of the oleanolic acid acetate, the salt thereof, the extract thereof or the fraction thereof contained in the composition is not particularly limited, but may be prepared to have 0.0001% by weight to 10% by weight, preferably 0.001% by weight to 1% by weight with respect to the total weight of the composition.

As used herein the term "pharmaceutically acceptable salt" refers to a salt having the form that can be used pharmaceutically among salts in which the cation and the anion are bound by the electrostatic attraction and may generally include metal salts, salts with organic bases, salts with inorganic acids, salts with organic acids, salts with basic or acidic amino acids, and the like. Examples of the pharmaceutically acceptable salt include metal salts such as alkaline metal salts (sodium salt, potassium salt, etc.), alkaline earth metal salts (calcium salt, magnesium salt, barium salt, etc.), aluminum salt, etc.; salts with organic salts such as triethylamine, pyridine, picoline, 2,6-lutidine, ethanolamine, diethanolamine, triethanolamine, cyclohexylamine, dicyclohexylamine, N,N-dibenzylethylenediamine, etc.; salts with inorganic acids such as hydrochloric acid, hydrobromic acid, nitric acid, sulfuric acid, phosphoric acid, etc.; salts with organic acids such as formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc.; salts with basic amino acids such as arginine, lysine, ornithine, etc.; and salts with acidic amino acids such as aspartic acid, glutamic acid, etc.

The composition including the compound of the chemical formula I or a pharmaceutically acceptable salt thereof of the present invention may be formulated in the form of oral preparations such as a powder, a granule, a tablet, a capsule, a suspension, an emulsion, a syrup and an aerosol and an external preparation, a suppository and a sterilized injection solution according to each conventional method. In the present invention, carriers, excipients and diluents that can be included in the composition including adzuki beans extract and fraction may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. The composition can be formulated using a diluent or excipient such as a filler, an extender, a binder, a wetting agent, a disintegrant and a surfactant is commonly used in the formulation. Solid formulations for oral administration include a tablet, a pill, a powder, a granule, a capsule and the like. Such solid formulations may be prepared by mixing the adzuki beans extract and fraction thereof with at least one excipient, e.g., starch, calcium carbonate, sucrose, lactose, or gelatin. Also, a lubricant such as magnesium stearate or talc may be used in addition to a simple excipient. Examples of the liquids for oral administration include a suspension, an internal solution, an emulsion, and a syrup, and the liquids may further include various types of excipient including a wetting agent, a sweetener, a flavoring agent and a preservative, in addition to a simple diluent such as water or liquid paraffin. Examples of formulations for parenteral administration may include a sterilized aqueous solution, a non-aqueous solvent, a suspension, an emulsion, a lyophilized preparation, and a suppository. Examples of the non-aqueous solvents and the suspensions include propylene glycol, polyethylene glycol, vegetable oil including olive oil, and injectable esters including ethyl oleate. Bases for the suppositories may be witepsol, macrogol, tween 61, cacao butter, Laurin, or glycerogelatin.

The preferred dosage of the pharmaceutical composition of the present invention varies depending on the condition and the weight of the patient, the degree of disease, the type of drug, the administration route and the period of time, but can be appropriately selected by those skilled in the art. However, the oleanolic acid acetate of the present invention is preferably administered at a dose of 0.0001 mg/kg to 100 mg/kg, preferably 0.001 mg/kg to 100 mg/kg per day, for effective prevention or treatment. Further, the composition may be administered once a day, or administered in divided doses.

The pharmaceutical composition of the present invention may be administered to a mammal including rat, mouse, livestock, human via various routes. All manners of administration may be expected, and for example, the composition is administered by oral, rectal, intravenous, intramuscular, subcutaneous, intra-uterine or intracerebroventricular injections.

As used herein, the term "TNF-α" refers to a kind of inflammatory cytokine as an abbreviation of tumor necrosis factor.

As used herein, the term "IL-6" refers to a kind of an inflammatory cytokine as an abbreviation of interleukin-6.

As used herein, the term "COX-2" refers to prostaglandin $E_2$ ($PGE_2$) synthetase as an abbreviation of cyclooxygenase-2.

As used herein, the term "MCP-1" refers to a kind of an inflammatory chemokine as an abbreviation of monocyte chemoattractant protein-1.

As used herein, the term "adzuki bean" refers to a seed of *Phaseoli angularis* Wight belonging to the family Leguminosae. It has morphological traits of slightly flat, an oblate shape, and its seed coat is reddish brown, smooth and glossy. In terms of pharmacological actions, it has been used in the folk medicine for the treatment of diuretic, anti-inflammatory, anti-ulcer, antipyretic, anasarca, hepatocirrhosis, jaundice, abscess, purulent disease, dropsy, beriberi, diabetes, dysenteric diarrhea or the like. With respect to the objects of the present invention, the adzuki bean refers to the seed of *Phaseoli angularis* Wight or *Phaseolus calcaratus* Roxburgh, but is not limited thereto.

As used herein, the term "adzuki bean extract" refers to an extract obtained by extracting adzuki beans. With respect to the objects of the present invention, the adzuki bean extract may be a resultant that is obtained by extracting an adzuki bean crushed product using water, alcohol having 1 to 6 carbon atoms (methanol, ethanol, butanol, etc.) or a solvent mixture thereof, but is not limited thereto, and the resultant includes all of a liquid extract, a diluted or concentrated liquid extract, a dry product obtained by drying the liquid extract, or a crude purified product or purified product thereof.

According to one embodiment of the present invention, the adzuki bean crushed product may be extracted by using about 2-fold to 20-fold, preferably, 3-fold to 5-fold volume, with respect to dried product weight thereof, of water, a polar solvent, for example, C1 to C6 alcohol such as methanol, ethanol, butanol, or the mixtures thereof in a ratio of approximately 1:0.1 to 1:10 as an elution solution at an extract temperature ranging from 20° C. to 100° C., preferably room temperature, for an extract period ranging from about 12 hours to 4 days, preferably 3 days, by an extract method such as hot water extraction, cold-immersion extraction, reflux cold extraction or sonication. Preferably, it may be continuously extracted by cold-immersion extraction once to 5 times, and then filtered under reduced pressure, and the filtrate is concentrated at 20° C. to 100° C., preferably room temperature under reduced pressure using a rotary vacuum evaporator to obtain an adzuki bean (*Phaseoli angularis* Wight and *Phaseolus calcaratus* Roxburgh) crude extract that is solubilized in water, lower alcohol, or a solvent mixture thereof.

As used herein, the term "fraction" refers to a resultant that is obtained by a fractionation method for separating particular components or particular groups from a mixture containing various components. In the present invention, the fraction may be preferably a resultant that is obtained by fractionating the adzuki bean extract by a solution fractionation method using a solvent such as n-hexane, ethyl acetate or the like, and include all of a polar solvent fraction and a non-polar solvent fraction. Specifically, all of the hexane fraction, the ethyl acetate fraction and the water fraction may be used.

According to one embodiment of the present invention, the adzuki bean crude extract thus obtained is suspended in distilled water, and then a non-polar solvent such as hexane or ethyl acetate is added thereto in a volume of about 1 to 100-fold, preferably about 1 to 5-fold volume of the suspension so as to extract and separate a non-polar solvent soluble layer once to ten times, and preferably twice to five times. A typical fractionation process may be further performed (Harborne J. B. Phytochemical methods: A guide to modern techniques of plant analysis, 3rd Ed. p 6-7, 1998). Specifically, the adzuki bean crude extract is suspended in water, and then continuously extracted using an equal volume of n-hexane and ethyl acetate solvent so as to obtain each solvent soluble adzuki bean extract. More specifically, the adzuki bean crude extract is suspended in water and then mixed with an equal amount of n-hexane, followed by fractionation to obtain an n-hexane soluble fraction and a water-soluble fraction. Ethyl acetate was added to this water-soluble fraction to obtain an ethyl acetate soluble fraction and a water-soluble fraction.

According to another embodiment of the present invention, provided is a health functional food for preventing or improving drug-induced nephrotoxicity, including oleanolic acid acetate, which is a compound represented by the chemical formula I or a sitologically acceptable salt thereof as an active ingredient.

Since the compound of chemical formula I of the present invention is derived from the natural product, and its safety has been approved, it can be used as a food composition. The oleanolic acid acetate or sitologically acceptable salt thereof may be included in an amount of 0.01% by weight to 100% by weight and more preferably 1% by weight to 80% by weight, with respect to the total weight of the food composition. If the food is a drink, it may be included in an amount of 1 g to 30 g, preferably 3 g to 20 g, with respect to 100 ml. In addition, the composition may further include additive ingredients capable of augmenting smell, taste, look, etc. which are commonly used in food compositions. For example, vitamins A, C, D, E, B1, B2, B6, and B12, niacin, biotin, folate, pantothenic acid or the like may be included. Further, minerals such as zinc (Zn), iron (Fe), calcium (Ca), chrome (Cr), magnesium (Mg), manganese (Mn), copper (Cu) or the like may be included. Further, amino acids such as lysine, tryptophan, cysteine, valine or the like may be included. Further, food additives such as preservatives (potassium sorbate, sodium benzoate, salicylic acid, sodium dehydroacetate, etc.), germicides (bleaching powder and high-grade bleaching powder, sodium hypochlorite, etc.), antioxidants (butylated hydroxy anisole (BHA), butyl hydroxy toluene (BHT), etc.), the colorant (tar color, etc.), color fixatives (sodium nitrite, sodium nitrite, etc.), bleaching agents (sodium sulfite), seasonings (MSG, sodium glutamate, etc.), sweeteners (dulcin, cyclamate, saccharin, sodium, etc.), flavors (vanillin, lactones, etc.), blowing agents (alum, D-potassium hydrogen tartrate, etc.), enhancers, emulsifiers, thickeners (thickening agents), coating agents, chewing gum bases, anti-foaming agents, solvents, conditioners, may be added. These additives are selected according to the type of food, and used in a proper amount.

As used herein, the term "sitologically acceptable salt" refers to a salt that can be sitologically used among salts in which the cation and the anion are bonded to each other by electrostatic attraction. Specific examples thereof include examples of the above-mentioned "pharmaceutically acceptable salt."

As used herein, the term "health food" refers to a food that positively maintains or improves health compared to general food, and the term "health supplement food" refers to food to be used as a health supplement. In some cases, the terms "functional food," "health food" and "health supplement food" are used interchangeably with each other. The food can be prepared in various forms such as a tablet, a capsule, a powder, a granule, a liquid, a pill, etc., so as to provide a useful effect.

As used herein, the term "functional food" is the same term as food for special health use (FoSHU) and means food having high medicinal and medical effects, which is processed to effectively exert a body-regulating function and to supply nutrients.

As specific examples of the health functional food, the composition is used to provide processed foods that are modified to have improved storage while maintaining properties of agricultural products, livestock products or marine products. The health functional food including the composition may be, but is not particularly limited to, preferably those prepared in the form of margarines, fat continuous or water continuous or bicontinuous spreads, fat reduced spreads, confectionery products such as chocolate or chocolate coatings or chocolate fillings or bakery fillings, ice creams, ice cream coatings, ice cream inclusions, dressings, mayonnaise, cheeses, cream alternatives, dry soups, drinks, cereal bars, sauces, snack bars, dairy products, clinical nutrition products and infant formulations.

According to another embodiment of the present invention, provided is an anticancer adjuvant for preventing or treating anticancer drug-induced nephrotoxicity, including oleanolic acid acetate, which is a compound represented by the chemical formula I, or a pharmaceutically acceptable salt thereof as an active ingredient.

The anticancer adjuvant may be used in combination with conventional anticancer drugs such as cisplatin, carboplatin, oxaliplatin, nedaplatin, doxorubicin, taxol, tamoxifen, camtobell, adrucil, glivec, etoposide, zometa, oncovin, thereby reducing the nephrotoxicity to improve the anticancer efficacy.

According to one embodiment of the present invention, mice exposed to cisplatin shows a decrease in body weight and kidney organs, resulting in nephrotoxicity. Thus, the mortality rate is 100%. However, in the group administered with cisplatin and oleanolic acid acetate, the mortality is reduced to 44% (FIGS. 2A, 2B and 2C). In addition, BUN value in blood, a blood biochemical indicator indicating the blood content of urea nitrogen, which is a metabolic product of proteolysis, is significantly increased due to nephrotoxicity in the group treated with cisplatin but decreased in the group treated with cisplatin and oleanolic acid acetate. These results indicate that oleanolic acid acetate reduces BUN values increased by cisplatin (FIG. 2D).

In another embodiment, the inflammatory cytokines TNF-α and IL-6 are significantly increased in the blood and kidney tissues in the cisplatin-treated group, and COX-2 and MCP-1 are significantly increased in the kidney tissues, but all of them are decreased in the group treated with a combination of cisplatin and oleanolic acid acetate. These results indicate that oleanolic acid acetate effectively inhibits the inflammatory reaction induced by cisplatin (FIGS. 3A, 3B, 4A, 4B, 4C and 4D).

Further, the present invention provides a method of treating drug-induced nephrotoxicity by administering to a patient a pharmaceutically effective amount of the oleanolic acid acetate or a pharmaceutically acceptable salt thereof. The treatment of nephrotoxicity refers to a therapeutic action such as reduction or improvement of damage to the kidney. As used herein, the term "effective amount" refers to the amount of oleanolic acid acetate or a pharmaceutically acceptable salt thereof that exhibits an effective therapeutic effect on drug-induced nephrotoxicity.

Further, the present invention provides a use of the oleanolic acid acetate or a pharmaceutically acceptable salt thereof in the preparation of the drug for the treatment of drug-induced nephrotoxicity.

Further, the present invention provides a composition including the oleanolic acid acetate or a pharmaceutically acceptable salt thereof for use in the treatment of drug-induced nephrotoxicity.

Further, the present invention provides a use of the oleanolic acid acetate or a pharmaceutically acceptable salt thereof for the treatment of drug-induced nephrotoxicity.

Further, the present invention provides a method of treating cancer by administering to a patient a pharmaceutically effective amount of the oleanolic acid acetate or a pharmaceutically acceptable salt thereof as the anticancer adjuvant and a pharmaceutically effective amount of a platinum-based anticancer drug. As an anticancer adjuvant, the oleanolic acid acetate or a pharmaceutically acceptable salt thereof can achieve effective treatment of cancers by reducing and improving the anticancer drug-induced nephrotoxicity.

Further, the present invention provides a use of the oleanolic acid acetate or a pharmaceutically acceptable salt thereof in the preparation of the anticancer adjuvant.

Further, the present invention provides a composition including the oleanolic acid acetate or a pharmaceutically acceptable salt thereof for a use as an anticancer adjuvant.

Further, the present invention provides a use of the oleanolic acid acetate or a pharmaceutically acceptable salt thereof for an anticancer adjuvant.

The description mentioned for the use, composition and treatment method of the present invention are applied equally unless they are mutually contradictory.

The oleanolic acid acetate of the present invention is derived from a natural product, has no side effects and no cytotoxicity, and has excellent effects of preventing, improving and treating nephrotoxicity caused by a drug, particularly a platinum-based anticancer drug, so that it can be utilized as a pharmaceutical composition, a health functional food, and a cancer adjuvant thereof.

More specifically, the oleanolic acid acetate of the present invention significantly inhibits the renal function index BUN values, inflammatory cytokine level in blood, and inflammatory factor expression level in kidney tissue in an animal model in which acute renal failure is induced by a platinum-based anticancer drug so that it has excellent effects of inhibiting nephrotoxicity to be effective in preventing, improving and treating nephrotoxicity effectively.

Figure 1A:
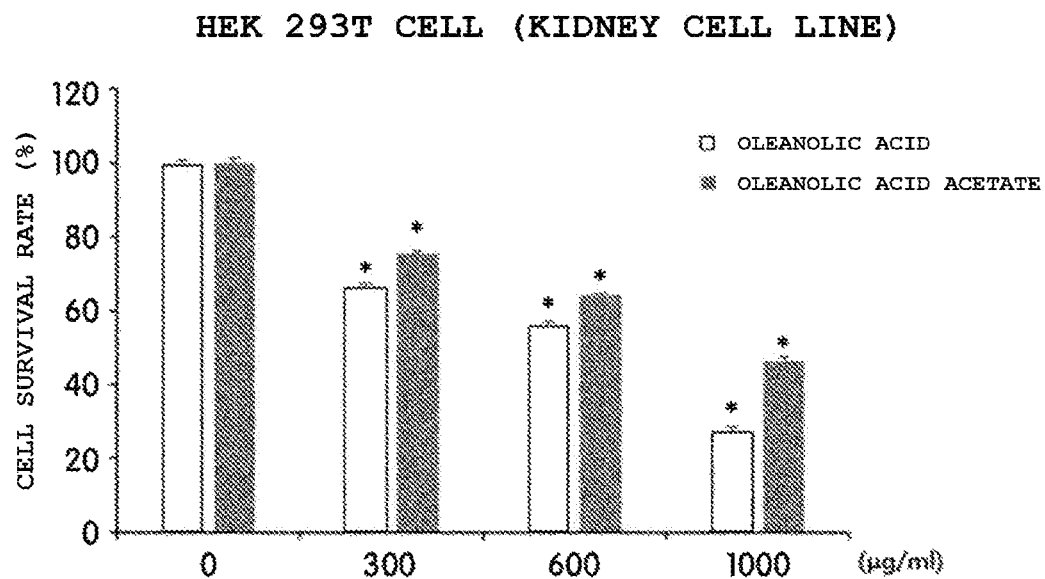
FIG. 1 shows results of MTT assay to show the cytotoxicity comparative evaluation between oleanolic acid and oleanolic acid acetate in HEK-293T cells, human embryonic kidney cells, (FIG. 1A), abdominal macrophages (FIG. 1B), and spleen cells (FIG. 1C) (*: $p<0.05$ significance with the control group).

Hereinafter, the present invention will be described in more detail with reference to examples. However, these examples are for illustrative purposes only, and the scope of the present invention is not limited to these examples.

Example 1: Preparation of Adzuki Bean Ethanol Extract and Separation and Purification of Compound of the Chemical Formula I Example 1-1: Preparation of Adzuki Bean Extract Adzuki beans (*Phaseoli angularis* Wight or *Phaseolus calcaratus* Roxburgh) were washed with water, dried in the shade, and then pulverized in a waring blender. 20 kg of the pulverized adzuki bean was put in 100 L of methanol, and cold-immersion extraction was performed at room temperature for 3 days. A filter paper (Whatman, USA) was used to perform filtration under reduced pressure, and the methanol solvent was removed from the filtered extract using a rotary vacuum evaporator at room temperature, so as to prepare 450 g of adzuki bean extract as an extraction residue.

Example 1-2: Preparation of Fraction

In order to isolate an active fraction from the prepared adzuki bean extract, adzuki bean extract was suspended in 1 L of water, and an equal volume of n-hexane was added thereto, and mixed, followed by fractionation. This procedure was repeated four times to obtain 1 L of a water-soluble fraction and 4 L of n-hexane soluble fraction. Subsequently, the n-hexane soluble fraction was concentrated under reduced pressure to obtain 50 g of n-hexane soluble extract.

Further, an equal volume of ethyl acetate was added to 1 L of the water-soluble fraction, and mixed with each other, followed by fractionation. This procedure was repeated three times to obtain 1 L of a water-soluble fraction and 3 L of ethyl acetate soluble fraction.

The ethyl acetate soluble fraction thus obtained was concentrated under reduced pressure so as to obtain 35 g of an ethyl acetate soluble extract, and the remaining water-soluble fraction was concentrated under reduced pressure to obtain 35 g of concentrate for a water fraction.

Example 1-3: HPLC Analysis of Adzuki Bean Extract and Fraction

Each of the adzuki bean extracts and fractions obtained in Examples 1-1 and 1-1-2 was subjected to HPLC analysis.

In this regard, Agilent Technologies 1200 series was used for HPLC, and YMC J'sphere ODS-H80 (YMC, 4 μm, 4.6 mm I.D.×150 mm) column was used as an analysis column. At this time, 5% to 90% $CH_3CN$ was applied as an analysis solvent at a flow rate of 1 ml/min, and analysis was performed at 210 nm and 10 μl of the sample was injected (Table 1).

TABLE 1

| Time | Solvent (%) | |
|---|---|---|
| (minutes) | $CH_3CN$ | $H_2O$ |
| 0 | 5 | 95 |
| 15 | 5 | 95 |
| 25 | 30 | 70 |
| 30 | 30 | 70 |
| 50 | 90 | 10 |
| 70 | 90 | 10 |

The peaks of catechin-7-glucopyranoside (catechin-7-glu), rutin, oleanolic acid acetate (OAA) and stigmasterol were observed at 5.5, 24.5, 35.5, and 35.5 minutes, respectively, and HPLC chromatograms of *Phaseoli angularis* Wight and *Phaseolus calcaratus* Roxburgh showed a similar pattern.

Example 1-4: Purification of Active Ingredient 80 g of the n-hexane fraction obtained in Example 1-2 was applied to silica gel column chromatography using a step gradient solvent system consisting of hexane:ethyl acetate (100:1->1:1) to obtain 5 active fractions (Fr.1-5). Recrystallization was performed by adding methanol to Fraction 3 and Fraction 4 among the active fractions, thereby purifying 2 types of compounds as a white powder.

The 2 types of compounds thus purified were applied to instrumental analysis (1H-, 13C-NMR, MS) and reference values (Voutquenne L. et al. Phytochemistry 2003, 64, 781-789; Kongduang D. et al. Tetrahedron letters 2008, 49, 4067-4072) to identify oleanolic acid acetate (chemical formula I), respectively.

Chemical Formula I

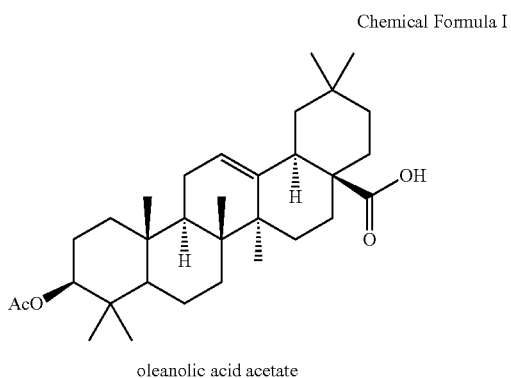

oleanolic acid acetate

4aS,6aR,6aS,6bR,8aR,10S,12aR,14bS-10-hydroxy-2,2, 6a,6b,9,9,12a-heptamethyl-1,3,4,5,6,6a,7,8,8a,10,11,12,13, 14b-tetradecahydropicene-4a-carboxylic acid acetate Example 2: Comparison of Cytotoxicity Between Oleanolic Acid and Oleanolic Acid Acetate In order to compare the cytotoxicity of oleanolic acid and oleanolic acid acetate, human kidney cell lines, mouse peritoneal macrophages, and spleen primary cells were used.

Example 2-1: Culture of Cell Lines and Separation of Primary Cells

HEK-293T cells, human embryonic kidney cells, were cultured in Dulbecco's modified eagle medium (Cat No. 12800-017, Gibco, USA) supplemented with heat-inactivated 10% FBS.

For the isolation of peritoneal macrophage of mice, 3 ml of 3% thioglycollate medium was administered intraperitoneally to 5-6 week old ICR male mice (Oriental Bio, Seoul, Korea). After 3 days, 6 ml to 7 ml of PBS was administered intraperitoneally, followed by a massage of peritoneal cavity to collect the peritoneal fluid. The collected peritoneal fluid was centrifuged and suspended in RPMI (10% FBS, 1% antibiotics), transferred to a plate, and stabilized at 37° C. for 2 hours.

For the isolation of mouse spleen cells, 5-6 week old ICR male mice (Oriental Bio, Seoul, Korea) were sacrificed with $CO_2$ and then their spleen was aseptically extracted. The spleen was ground with a filter to separate single spleen cells, centrifuged using centrifugation, and erythrocytes were dissolved using ficoll. Cells from which erythrocytes had been removed were stabilized with RPMI (10% FBS, 1% antibiotics) at 37° C. for 2 hours.

Example 2-2: Evaluation of Cytotoxicity

The survival rate of cultured cells was measured by MTT reduction method. As an MTT solution, formazan was formed by mitochondrial dehydrogenases in living cells to confirm cell viability. In order to confirm the cytotoxicity, cells were cultured in a 96-well plate at $5\times10^4$ cells/well at 37° C., followed by treatment with oleanolic acid and oleanolic acid acetate per concentration thereof, and the cells were cultured for 24 hours. After 24 hours, 20 µl of MTT solution was added to each well, followed by further culturing for 2 hours. Then, the culture solution was removed, and 100 µl of dimethylsulfoxide was added thereto. The absorbance thereof was measured at 570 nm.

Example 2-3: Comparison of Cytotoxicity

In order to evaluate the cytotoxicitiy of oleanolic acid and oleanolic acid acetate, MTT assay was performed using human kidney cell lines, peritoneal macrophage, and spleen cells. As a result, the cytotoxicity of oleanolic acid acetate was concentration-dependently less than that of oleanolic acid in human kidney cell lines. Oleanolic acid and oleanolic acid acetate, respectively, were found to have a cell survival rate of 27% and 43% at the highest concentration of 1000 µg/ml, indicating that oleanolic acid acetate induced less cytotoxicity (FIG. 1A).

Figure 1B:
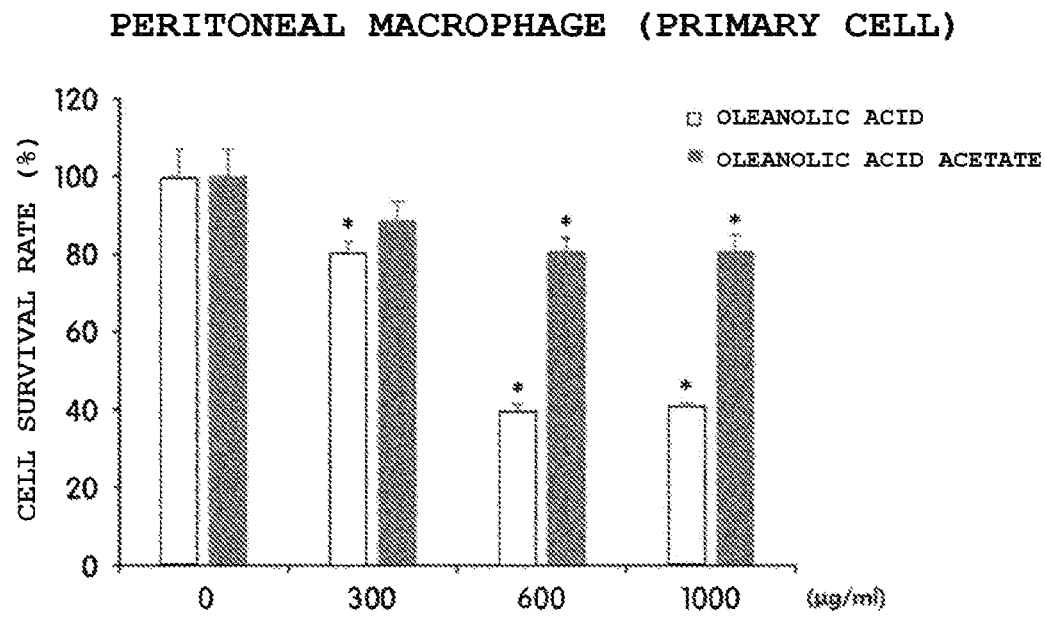

In peritoneal macrophages collected from mouse peritoneal cavity, oleanolic acid showed cytotoxicity in a concentration-dependent manner, while oleanolic acid acetate showed a cell survival rate of 81% at the maximum concentration of 1000 µg/ml, indicating almost no cytotoxicity. In addition, the cell survival rate of 81% at 1000 µg/ml of oleanolic acid acetate was found to be about twice that of 41% of the oleanolic acid (FIG. 1B).

Figure 1C:
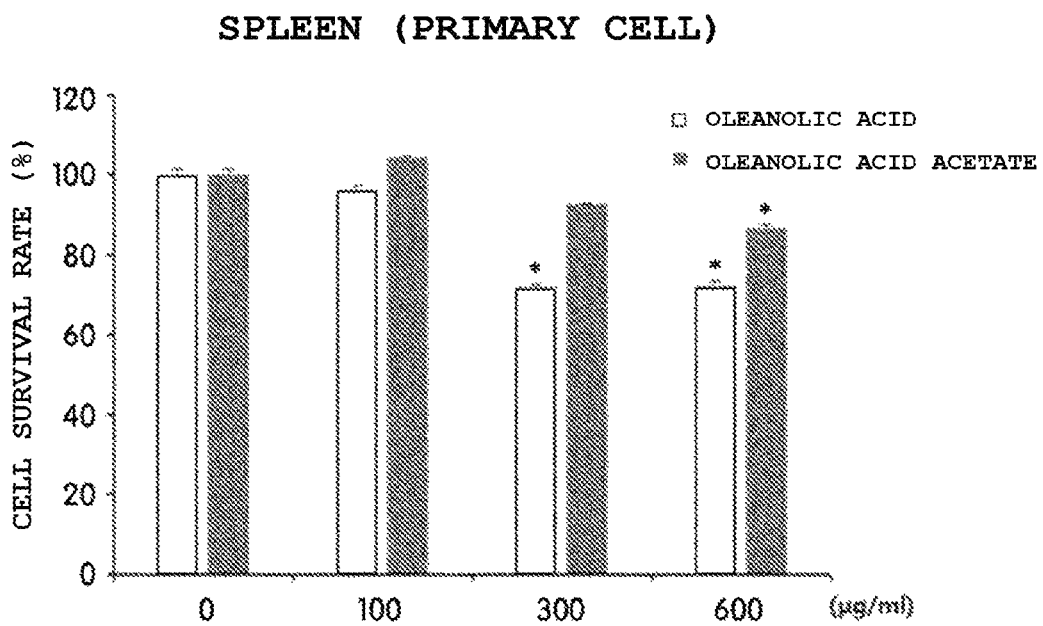

In the spleen cells isolated from the mouse spleen, oleanolic acid acetate had higher cell survival rate than that of oleanolic acid at all concentrations (100, 300, and 600 µg/ml), resulting in less cytotoxicity (FIG. 1C).

Example 3: Inhibitory Effect of Oleanolic Acid Acetate on Nephrotoxicity in Cisplatin-Induced Nephrotoxicity Animal Model In order to examine the inhibitory effect of oleanolic acid acetate on cisplatin-induced nephrotoxicity, animal experiments were conducted.

Example 3-1: Cisplatin-Induced Nephrotoxicity 8 week old C57BL/6 male mice having a weight of 20 g to 25 g (Oriental Bio, Seoul, Korea) were purchased and randomly divided into saline-treated group (Control, CON), oleanolic acid acetate-treated group (OAA), only cisplatin-treated group (CP) and cisplatin and oleanolic acid acetate-treated group (CP+OAA). For the experiment, the mice were kept under constant temperature (23±3° C.), humidity (55±15%) and light irradiation (7:00 to 19:00). After the purchase, the mice were stabilized in the SPF animal breeding room for 1 week and used in the experiment. Cisplatin (Sigma, St. Louis, Mo., USA) was dissolved in physiological saline at a concentration of 2 mg/ml and then administered intraperitoneally at a dose of 20 mg/kg. Oleanolic acid acetate was dissolved in distilled water, and the mixture was orally administered at a dose of 50 mg/ml 1 hour before the cisplatin administration and 1, 3, and 5 days after the cisplatin administration. Mice in all groups were sacrificed on day 5 after the cisplatin administration.

Example 3-2: Monitoring of Body Weight, Kidney Weight, Death Rate and Analysis of BUN After the mouse sacrifice, the body weight was measured, the kidney was isolated, the blood was collected from the heart, and the blood urea nitrogen (BUN), a biochemical indicator related to nephrotoxicity, was measured. The collected mouse blood was centrifuged at 3000 rpm and 4° C. for 15 minutes using a centrifuge to separate the only serum, and the BUN was measured using an automatic analyzer (Fuji Dry-Chem NX500i, Tokyo, Japan).

Figure 2A:
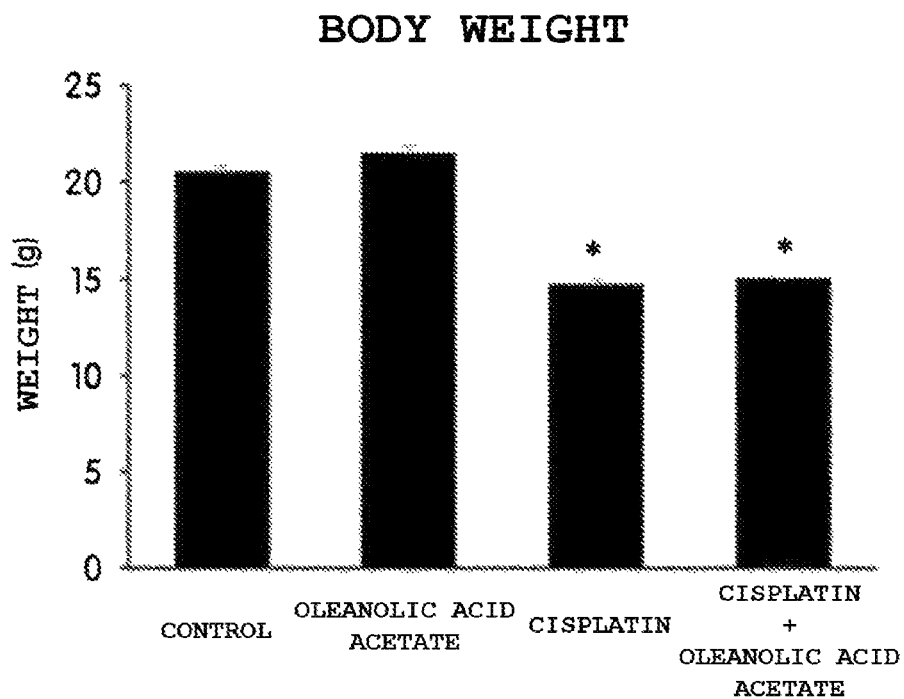
FIG. 2 shows changes in body weight (FIG. 2A), kidney tissue weight (FIG. 2B), death rate (FIG. 2C), and blood BUN value (FIG. 2d) after administration of oleanolic acid acetate at a concentration of 50 mg/Kg in cisplatin-induced nephrotoxicity animal experiments (*: $P<0.05$ significance with the control group, #: $p<0.05$ significance with only cisplatin-treated group).
Figure 2B:
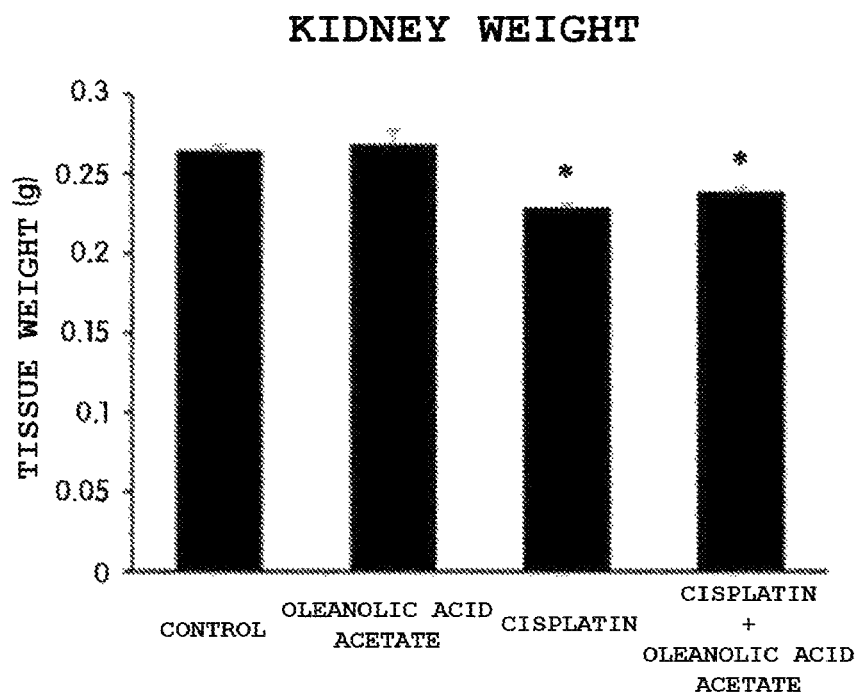
Figure 2C:
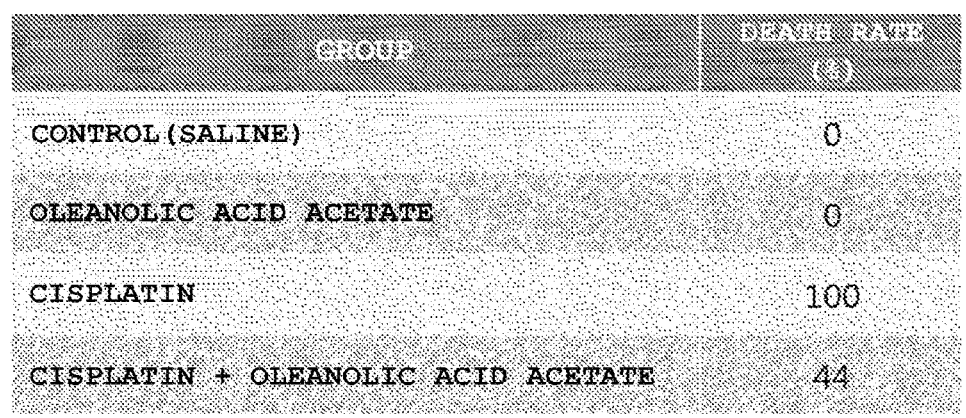

As shown in FIGS. 2A and 2B, in the case of mice exposed to cisplatin, the body weight and the kidney weight were decreased. The results indicate that the nephrotoxicity was induced. As shown in FIG. 2C, the death rate was 100% in the cisplatin-treated group, but the death rate was reduced to 44% in the cisplatin and oleanolic acid acetate-treated group. The death rate was expressed as a percentage by dividing the number of mice killed in each group by the total number of mice.

Figure 2D:
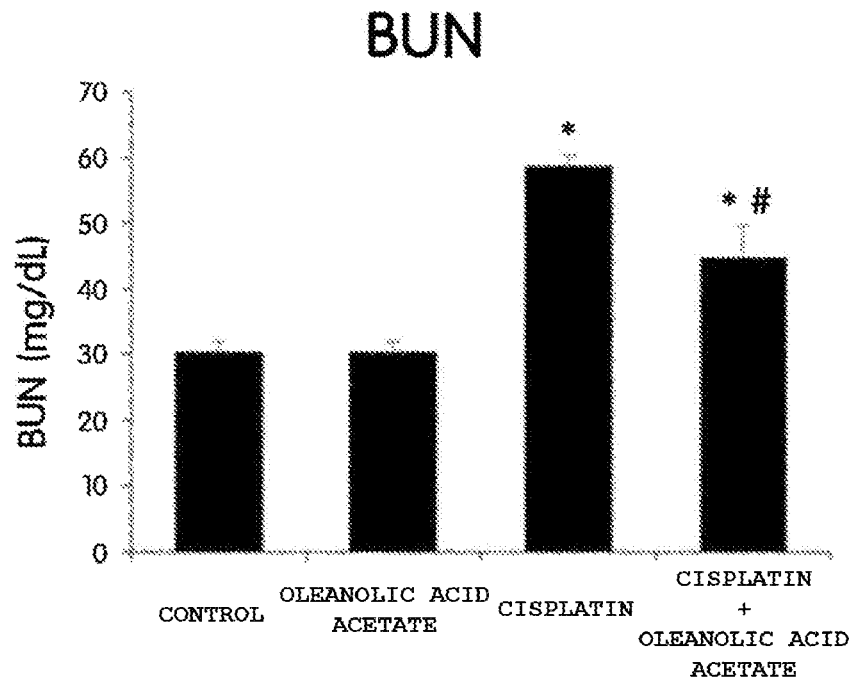

As shown in FIG. 2D, the BUN value is a blood biochemical indicator indicating the blood content of urea nitrogen, which is a metabolic product of proteolysis. Further, BUN elevation in blood generally indicates the presence of kidney disease. Accordingly, it was confirmed that the BUN value was significantly increased due to renal toxicity in the cisplatin-treated group, but the BUN value was decreased in the cisplatin and oleanolic acid acetate-treated group.

Example 3-3: Measurement of Inflammatory Cytokines (TNF-α, IL-6) in Blood

In order to measure inflammatory cytokines in the blood (TNF-α and IL-6), serum was separated and used from blood, and TNF-α and IL-6 were measured using a mouse ELISA kit (R&D system, Minneapolis, Minn., USA). ELISA color development was measured using a Varioskan™ LUX multimode microplate reader (Thermofisher, Sunnyvale, Calif., USA) at a wavelength of 450 nm.

Figure 3A:
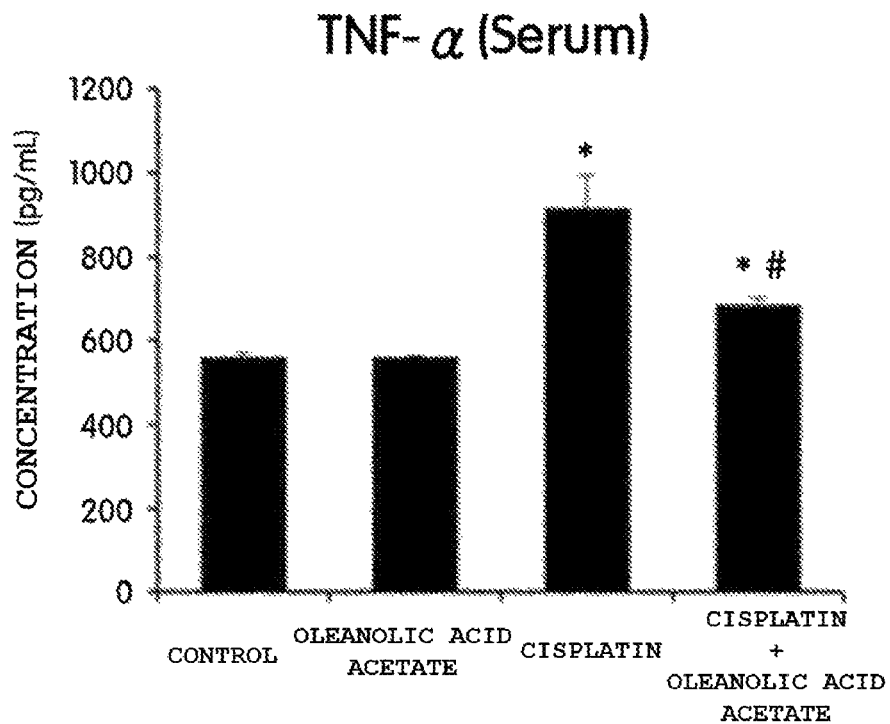
FIG. 3 shows changes in blood inflammatory cytokines TNF-α (FIG. 3A) and IL-6 (FIG. 3B) levels after administration of oleanolic acid acetate at a concentration of 50 mg/Kg in cisplatin-induced nephrotoxicity animal experiments (*: $P<0.05$ significance with the control group, #: $p<0.05$ significance with only cisplatin-treated group).
Figure 3B:
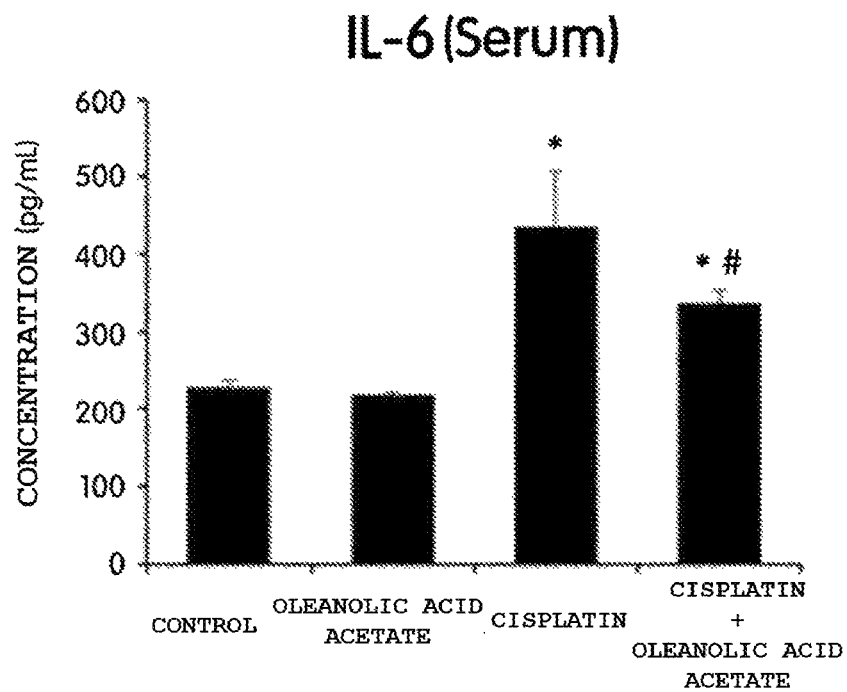
Figure 4A:
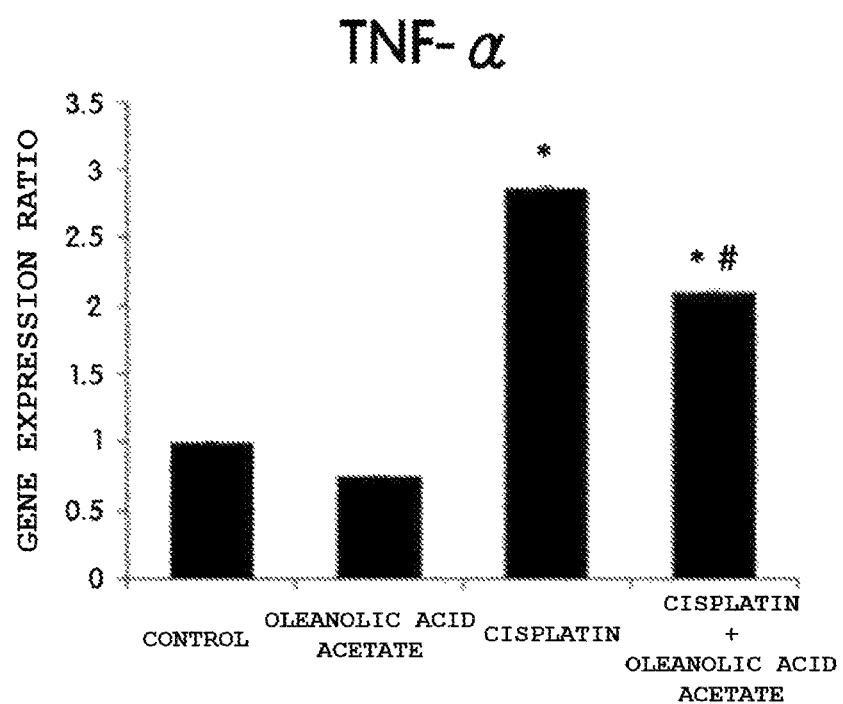
FIG. 4 shows changes in inflammatory cytokines in the kidney tissues TNF-α (FIG. 4A), IL-6 (FIG. 4B), COX-2 (FIG. 4C), and MCP-1 (FIG. 4D) expression levels after administration of oleanolic acid acetate at a concentration of 50 mg/Kg in cisplatin-induced nephrotoxicity animal experiments (*: $P<0.05$ significance with the control group, #: $p<0.05$ significance with only cisplatin-treated group).
Figure 4B:
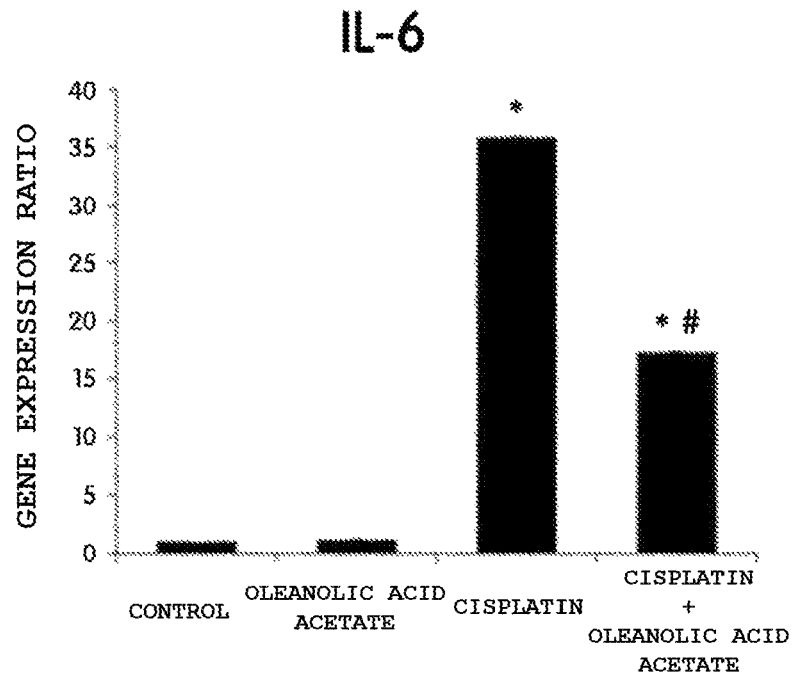
Figure 4C:
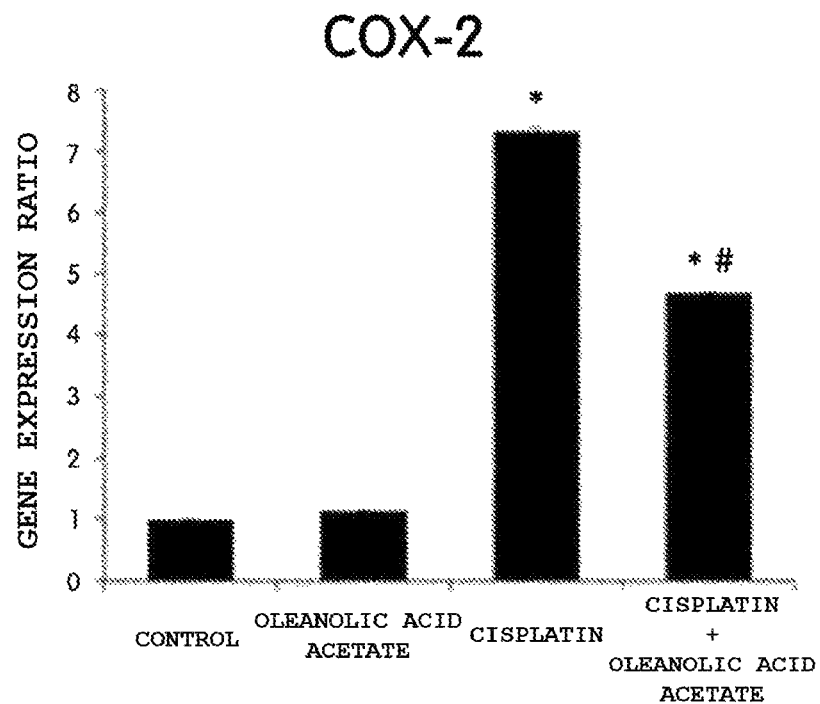
Figure 4D:
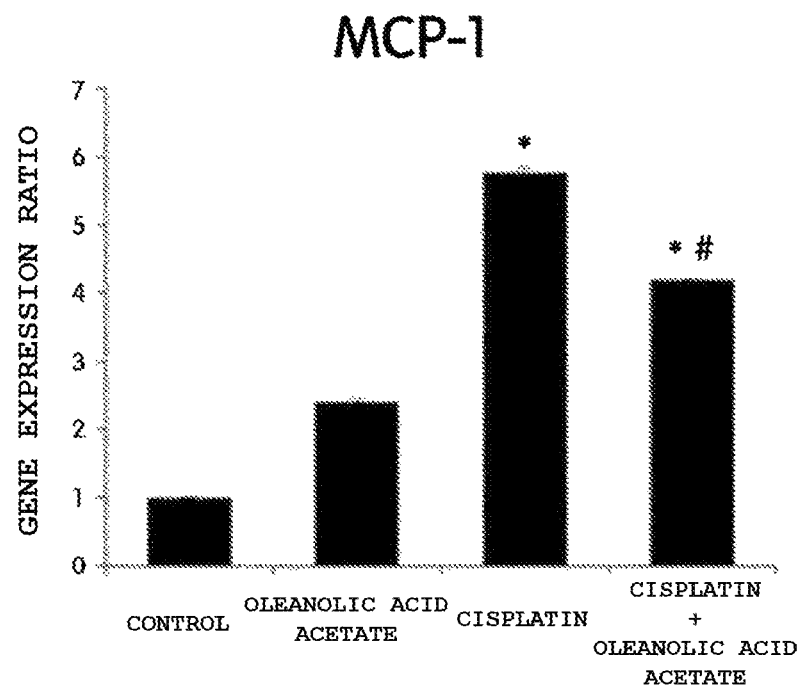

As shown in FIGS. 3A and 3B, TNF-α and IL-6, which are inflammatory cytokines in the blood, were significantly increased in the cisplatin-treated group, but TNF-α and IL-6 were decreased in the cisplatin and oleanolic acid acetate-treated group, indicating an effect of inhibiting the inflammatory response in the blood by nephrotoxicity.

Example 3-4: Analysis of Inflammatory Factor (TNF-α, IL-6, COX-2 and MCP-1) Expression in Kidney Tissue After the mouse sacrifice, kidneys were separated and homogenized by adding Trizol reagent (Invitrogen, Carlsbad, Calif., USA). To this, chloroform was added to extract RNA, and isopropanol was added to precipitate. After the RNA precipitate was washed with 75% ethanol, the RNA concentration and purity were measured with a 2100 Bioanalyzer System (Agilent Technologies, Santa Clara, Calif., USA), and Taqman reverse transcription reagents kit (Applied Biosystems, Foster City) was used to synthesize cDNA. The expression level of inflammatory factors was measured by real-time PCR using SYBR Green PCR master mix kit (Applied Biosystem, Foster City, Calif., USA).

In order to examine the expression levels of TNF-α and IL-6, inflammatory cytokines, COX-2, a prostaglandin $E_2$ ($PGE_2$) synthase involved in increasing the vascular permeability of the inflammatory response, and MCP-1, an inflammatory chemokine, Real-time PCR was performed on each gene. The results are shown in FIGS. 4A to 4D. As shown in FIGS. 4A to 4D, the amount of mRNA expression of TNF-α, IL-6, COX-2 and MCP-1 was significantly increased in the cisplatin-treated group, but the amount of mRNA expression of TNF-α, IL-6, COX-2 and MCP-1 was decreased in the cisplatin and oleanolic acid acetate-treated group, indicating an effect of inhibiting the inflammatory response in the blood by nephrotoxicity.

The sum of results suggests that oleanolic acid acetate inhibits the cisplatin-induced nephrotoxicity and effectively inhibits the expression and secretion of inflammatory factors. Furthermore, oleanolic acid acetate shows less cytotoxicity with excellent nephrotoxicity-inhibiting effect than oleanolic acid. Therefore, oleanolic acid acetate can be utilized as a pharmaceutical composition, health functional food, anticancer drug, etc. having an excellent effect of preventing, improving, treating nephrotoxicity without adverse effect in animals or human body.

Preparation Example 1: Preparation of Powder 0.1 g of oleanolic acid acetate, the adzuki bean extract including the same, or the fraction thereof, 1.5 g of lactose and 0.5 g of talc were mixed and filled in the air-tight bag to prepare a powder.

Preparation Example 2: Preparation of Tablet 0.1 g of oleanolic acid acetate, the adzuki bean extract including the same, or the fraction thereof, 7.9 g of lactose, 1.5 g of crystalline cellulose, and 0.5 g of magnesium stearate were mixed, and a 500 mg-tablet containing 50 mg of the active ingredient was prepared by a direct tableting method.

Preparation Example 3: Preparation of Powder 0.1 g of oleanolic acid acetate, the adzuki bean extract including the same, or the fraction thereof, 5 g of corn starch, and 4.9 g of carboxy cellulose were mixed well to prepare a powder, and 500 mg of the powder was put in a hard capsule to prepare a capsule.

Preparation Example 4: Preparation of Injectable Formulation

According to the conventional preparation method of injectable formulations, 2 ml-volume ampule for injection containing 0.1 g of oleanolic acid acetate, the adzuki bean extract including the same, or the fraction thereof, a proper amount of sterile distilled water for injection and a pH adjuster was prepared.

Preparation Example 5: Preparation of Liquid Formulation

According to the conventional preparation method of liquid formulations, 0.1 g of oleanolic acid acetate, the adzuki bean extract including the same, or the fraction thereof, 10 g of isomerized glucose syrup and 5 g of mannitol were added to and dissolved in purified water, and a proper amount of lemon flavor was added thereto. The ingredients were mixed, and then the total volume was adjusted to 100 ml by adding purified water. The mixture was filled in a brown bottle and sterilized to prepare a liquid formulation.

What is claimed is:
1. A method for treating drug-induced nephrotoxicity, the method comprising:
administering, to a patient, 0.001 mg/kg to 100 mg/kg per day of a compound represented by chemical formula I or a pharmaceutically acceptable salt thereof:

Chemical Formula I

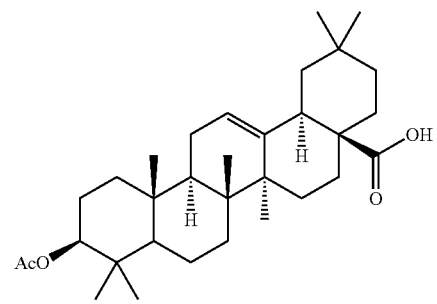

wherein the drug induced nephrotoxicity is induced by at least one platinum-based anticancer drug selected from the group consisting of cisplatin, carboplatin, oxaliplatin, and nedaplatin or antibiotic, wherein the compound or pharmaceutically acceptable salt thereof inhibits an inflammatory factor expression in kidney tissue wherein the inflammatory factor is a least one selected from the group consisting of TNF-α, IL-6, COX-2 and MCP-1.

2. The method of claim 1 for treating cisplatin-induced nephrotoxicity.

3. The method of claim 2 wherein the compound represented by the chemical of formula I or the pharmaceutically acceptable salt thereof is administered by parenteral administration of an aqueous solution.

4. The method of claim 2 wherein the compound represented by the chemical of formula I or the pharmaceutically acceptable salt thereof is administered through oral administration.

* * * * *